US007128571B2

(12) United States Patent
Young

(10) Patent No.: US 7,128,571 B2
(45) Date of Patent: Oct. 31, 2006

(54) ORTHODONTIC TOOL

(76) Inventor: Donald B. Young, 103-892 Central Street East, Prince George, British Columbia (CA) V2M 3B8

( * ) Notice: Subject to any disclaimer, the term of this patent is extended or adjusted under 35 U.S.C. 154(b) by 0 days.

(21) Appl. No.: 10/951,896

(22) Filed: Sep. 29, 2004

(65) Prior Publication Data
US 2006/0068352 A1 Mar. 30, 2006

(51) Int. Cl.
*A61C 7/00* (2006.01)
*A61C 3/00* (2006.01)
*B25B 13/22* (2006.01)

(52) U.S. Cl. .................... 433/3; 433/153; 81/129.5
(58) Field of Classification Search ................ 433/2, 433/3, 4, 153, 156–159, 161–163, 23; 81/126, 81/129.5
See application file for complete search history.

(56) References Cited

U.S. PATENT DOCUMENTS

| 1,166,766 | A |   | 1/1916  | Kelsey      |         |
|-----------|---|---|---------|-------------|---------|
| 1,215,442 | A |   | 2/1917  | Walker      |         |
| 1,261,339 | A |   | 4/1918  | Angle       |         |
| 1,276,678 | A | * | 8/1918  | Moore       | 81/134  |
| 1,531,898 | A |   | 3/1925  | Angle et al.|         |
| 2,027,470 | A | * | 1/1936  | Caruso      | 433/158 |
| 2,835,972 | A |   | 5/1958  | Sheldon     |         |
| 3,360,861 | A |   | 1/1968  | Hoffman     |         |
| 3,797,116 | A |   | 3/1974  | Meeks, Jr.  |         |
| 4,192,068 | A |   | 3/1980  | Wolfson     |         |
| 4,950,157 | A | * | 8/1990  | Cleary      | 433/4   |
| 5,529,489 | A |   | 6/1996  | Herrera     |         |
| 5,575,643 | A |   | 11/1996 | Green       |         |
| 2003/0224324 | A1 |   | 12/2003 | Dryer    |         |
| 2004/0048221 | A1 | * | 3/2004  | Jabri    | 433/2   |

* cited by examiner

*Primary Examiner*—Cary E. O'Connor
(74) *Attorney, Agent, or Firm*—Oyen Wiggs Green Mutala LLP

(57) ABSTRACT

A band seating tool is disclosed. The tool comprises a pair of curved claws for applying force to opposed sides of an orthodontic band. At least one of the claws may be translationally and/or pivotally moveable, such that the separation distance between the claws can be adjusted. Each claw preferably comprises a notch-shaped engagement feature for engaging the band and applying force thereto. The notches may comprise catch ledges for engaging the edges of the band and guide surfaces for engaging the outer surface of the band. In preferred embodiments, the band seating tools according to the invention comprise a bite-receiving member, such that the force associated with a patient's bite can be used to seat the band. The tool may also comprise an elongated safety portion which extends between the claws to protect the patient from injury.

34 Claims, 10 Drawing Sheets

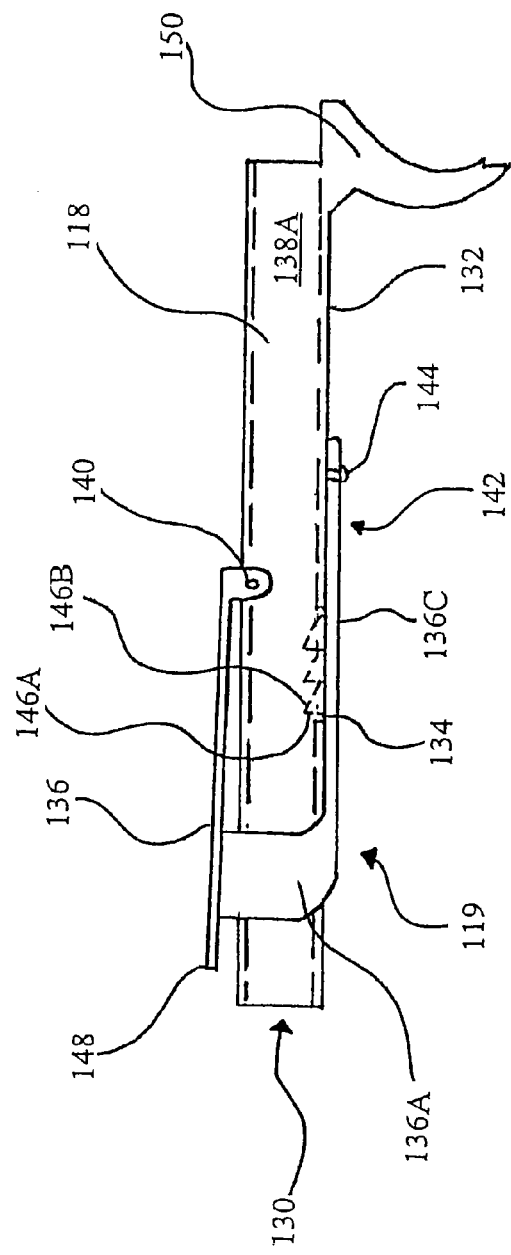
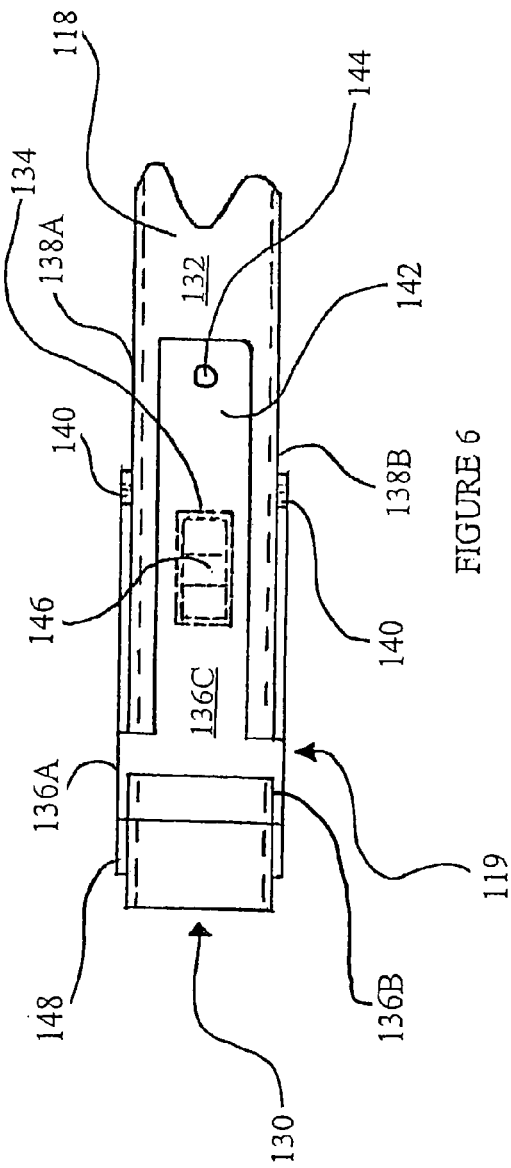

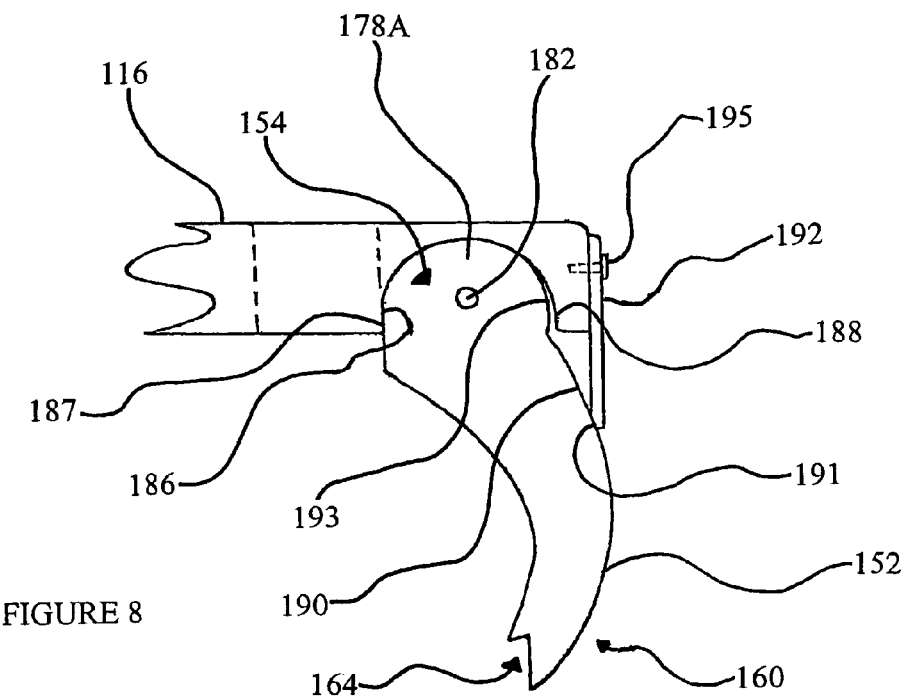
FIGURE 8
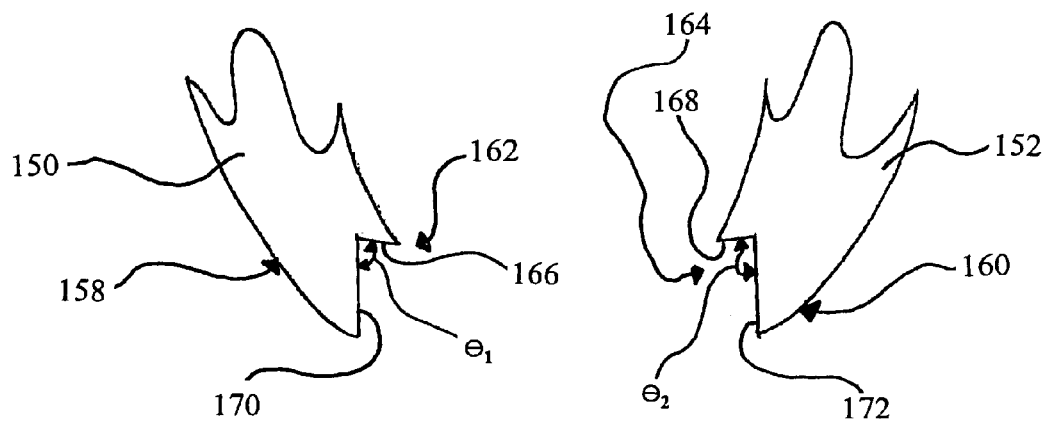
FIGURE 9A
FIGURE 9B

ORTHODONTIC TOOL

TECHNICAL FIELD

The invention relates to the field of orthodontics. Particular embodiments of the invention provide tools for use by orthodontists in seating bands on patients' teeth.

BACKGROUND

When installing braces or other orthodontic apparatus in a patient's mouth, orthodontists typically apply orthodontic bands to the patient's teeth. Orthodontic bands come in a variety of shapes a sizes to fit many variations of mandibular and maxillary molars and bicuspids. A typical orthodontic band 10 is shown in FIG. 1. Band 10 comprises a quasi-annular shaped piece of material with an inner surface 12, an outer surface 14 and upper and lower edges 16, 18. Typically, band 10 is typically formed from deformable and non-reactive materials, such as metals and metal alloys for example.

The application of an orthodontic band to a patient's tooth is commonly referred to as "seating" the band. Seating band 10 on a patient's tooth typically involves pushing band 10 over the tooth, such that inner surface 12 fits snugly against and circumferentially surrounds the outer surface of the tooth. Adhesive may be applied between inner surface 12 and the outer surface of the tooth to help secure band 10 to the tooth. Typically, the tooth does not perfectly match the outline of the chosen band 10 and, consequently, band 10 must be deformed as it is seated to conform its shape to that of the tooth. Seating an orthodontic band may require application of a considerable amount of force to deform the band and to push the band over the outer surface of the tooth.

Brackets or other orthodontic apparatus may be mounted or otherwise coupled to band 10. Orthodontic band 10 may incorporate various attachment features (not shown), which assist in coupling an orthodontic apparatus to the band. Bands 10 are often adapted to the shape of a tooth at a preliminary appointment, then sent on a model of the dental arch to an orthodontic lab for modification with various attachment features which may be welded or otherwise attached to band 10. The patient then returns to the orthodontist for final seating and cementation, where band 10 is affixed to the patient's tooth.

Because of the considerable amount of force required to seat orthodontic bands and because of the confined space within a patient's mouth, orthodontists usually use a tool to assist with seating orthodontic bands. Such tools are typically referred to as "band seaters" or "band seating tools." Band seating tools typically have an elongated shaft or handle, which the orthodontist uses to grip and manipulate the tool; and a post, which projects from an opposite end of the tool. While gripping the tool by the shaft or handle, the orthodontist typically seats a band on a tooth by pushing or otherwise forcing the band onto the tooth using the post of the band seating tool. Some known band seating tools allow a patient to bite down on the tool, so that, rather than the orthodontist applying force to the band through the band seating tool, the force required to seat the band is transferred from the patient's jaw through the handle and post of the seating tool and onto the band.

Prior art band seating tools are disclosed in:
U.S. Pat. No. 2,835,972 (Sheldon);
U.S. Pat. No. 3,360,861 (Hoffman);
U.S. Pat. No. 1,261,339 (Angle);
U.S. Pat. No. 4,192,068 (Wolfson); and
U.S. Pat. No. 3,797,116 (Meeks Jr.).

One drawback with prior art band seating tools is that their posts are often prone to slipping off of the relatively thin edge of the band when they are used to seat the band (see edge 16 of band 10 in FIG. 1). If this occurs, the post and/or other parts of the band seating tool may damage the patient's teeth and/or gingiva. This is particularly problematic in view of the considerable forces used to seat ;orthodontic bands. Another problem with many prior art band seating tools is that they have only one post. When an orthodontist uses a single post band seating tool to apply force to one side of a band, the band may slide around the outer surface of the tooth, unseating the opposing side of the band.

The prior art band seating tool disclosed in U.S. Pat. No. 3,797,116 (Meeks, Jr.) has a pair of posts which are used to apply force to opposing sides of an orthodontic band. However, these are straight posts, which are disposed at a fixed angle (relative to the shaft of the tool), such that the posts diverge from one another as they extend away from the shaft. This diverging angular orientation imports (to forces transferred through the posts to the band) force components that are oriented away from the outer surface of the tooth. These force components tend to increase the likelihood for either or both posts to slip off of the edge of the band, potentially injuring the patient. Further, when applying an orthodontic band such as band 10 to a mandibular tooth, the diverging posts of the Meeks Jr. tool would tend to spread the upper band edges 16, distorting them away from the tooth surface, rather than providing the close fit desired between the inner band surface 12 and the outer tooth surface. As the posts of the Meeks Jr. tool are fixed (not adjustable), a large selection of similar tools are required to accommodate variations in size and/or angulation of patient teeth.

This invention addresses the foregoing problems.

BRIEF DESCRIPTION OF THE DRAWINGS

In drawings which depict non-limiting embodiments of the invention:

FIG. 5 is a side elevation view of the adjustment assembly of the FIG. 2 band seating tool;

FIG. 6 is a bottom plan view of the FIG. 5 adjustment assembly;

FIG. 8 is a fragmented side elevation view showing the pivot joint which couples the FIG. 7B forward claw member with the shaft of FIGS. 3 and 4;

FIGS. 9A and 9B are respectively magnified fragmented side elevation views of the claw members of FIGS. 7A and 7B;

DETAILED DESCRIPTION

Figure 1:
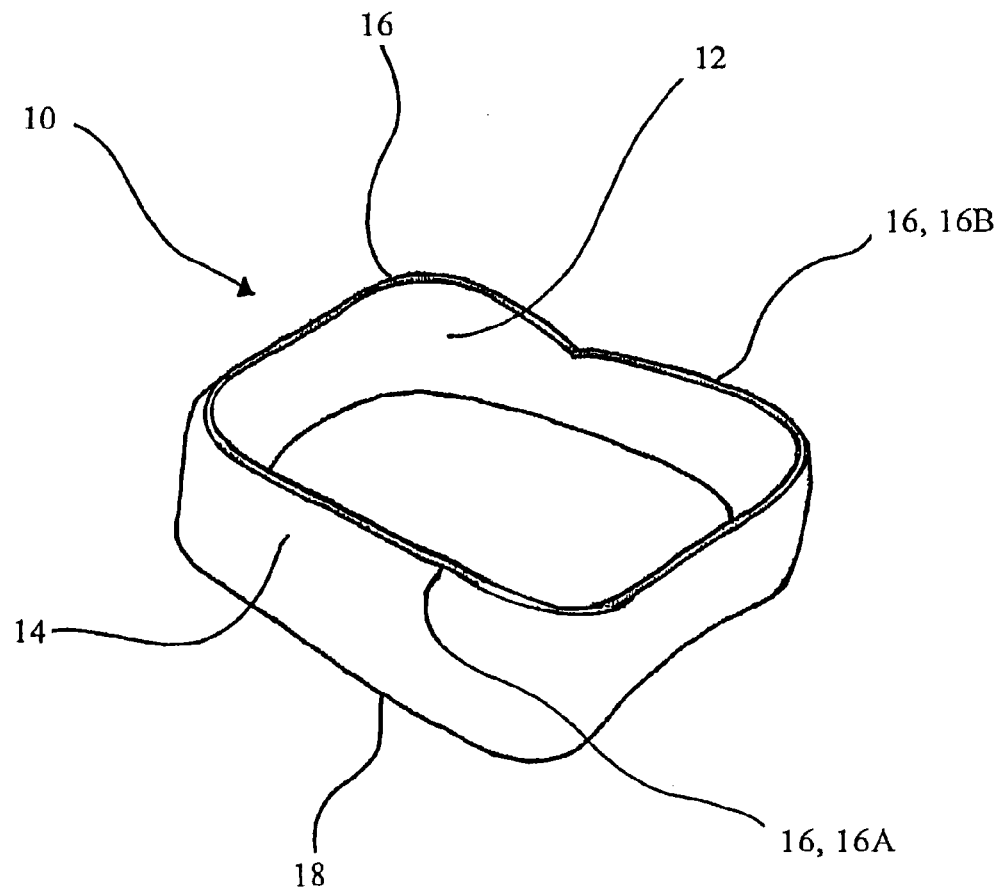
FIG. 1 is an isometric view of a typical prior art orthodontic band.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Band seating tools according to particular embodiments of the invention incorporate a pair of spaced apart claws having end portions which extend toward one another for applying force to an orthodontic band on opposite sides of a tooth. In some embodiments, the claws have concave shapes and are oriented such that their end portions curve toward one another. One or both of the claws may be translationally and/or pivotally moveable, such that the separation distance between the claws can be adjusted. Each claw preferably has a notch-shaped engagement feature for engaging an edge of the band and applying force thereto. The notches may comprise catch ledges for engaging an edge of the band and guide surfaces for engaging an outer surface of the band. Band seating tools according to the invention preferably have a bite-receiving member, such that the force associated with a patient's bite can be used to seat the band. The bite-receiving member may have an elongated safety portion which extends between the claws to protect the patient if the tool slips off of the band.

FIGS. 2–11 depict various views and components of a band seating tool 110 according to a particular embodiment of the invention. Tool 110 is a generally elongated device having a handle 112 at a first end thereof and a band seating assembly 114 at its opposing end. A shaft assembly 117 extends between handle 112 and band seating assembly 114. Band seating assembly 114 includes a pair of curved claws 150, 152, namely rearward claw 150 and forward claw 152, which are separated by a gap 156 and which may be concave-shaped. Shaft assembly 117 includes a shaft 116, which extends between handle 112 and band seating assembly 114; and an adjustment assembly 119, which fits slidably over shaft 116 to permit relative longitudinal movement between shaft 116 and adjustment assembly 119 and corresponding adjustment of the width of gap 156, as described below.

In this description and the accompanying claims:
(i) "rear," "rearward," "rearwardly" and similar words refer to locations that are closer to the handle end 120 of tool 110 than to the band seating assembly end 122 of tool 110 and/or to directions that extend from the band seating assembly end 122 of tool 110 toward the handle end 120 of tool 110 (see FIG. 2);
(ii) "front," "forward," "forwardly" and similar words refer to locations that are closer to the band seating assembly end 122 of tool 110 than to the handle end 120 of tool 110 and/or to directions that extend from the handle end 120 of tool 110 toward the band seating assembly end 122 of tool 110;
(iii) "longitudinal," "longitudinally" and similar words refer to directions which extend generally between the handle end 120 of tool 110 and the band seating assembly end 122 of tool 110 (or vice versa);
(iv) "transverse," "transversely" and similar words refer to directions that are generally orthogonal to the longitudinal direction as illustrated by double-headed arrow 111 of FIG. 2; and
(v) "vertical," "vertically" and similar words refer to directions that are generally orthogonal to planes defined by the longitudinal and transverse directions, as shown by double-headed arrow 113 of FIG. 2.

Those skilled in the art will appreciate that these and other directional conventions are used as a matter of convenience in this description and the accompanying claims and that the actual directions associated with tool 110 depend on its specific orientation. Accordingly, such directional terms are not strictly defined and should not be interpreted narrowly.

Handle 112 is preferably fabricated from or coated with a soft, ergonomic material, such as plastic or rubber for example. The surfaces of handle 112 may include grips, such as grooves 124 to assist the orthodontist in firmly gripping tool 110. Alternative grips, such as transversely oriented grooves, longitudinally or transversely oriented protrusions, etc. may be provided.

Shaft 116 is coupled to handle 112. Preferably, at least a rearward portion of shaft 116 is rectangular in cross-section and is received in a correspondingly shaped recess (not shown) in handle 112. This shape of shaft 116 inhibits rotation of shaft 116 with respect to handle 112 due to torques imparted on end 122 of tool 110 while seating a band. Shaft 116 may be longitudinally grooved or have other cross-sectional shapes, such as circular, oval or polygonal for example. Preferably, shaft 116 is fabricated from a suitable metal or metal alloy, such as stainless steel or titanium. Shaft 116 and other components of tool 110 are preferably fabricated from materials resistant to corrosion or other deterioration from routine sterilization techniques.

Figure 3:
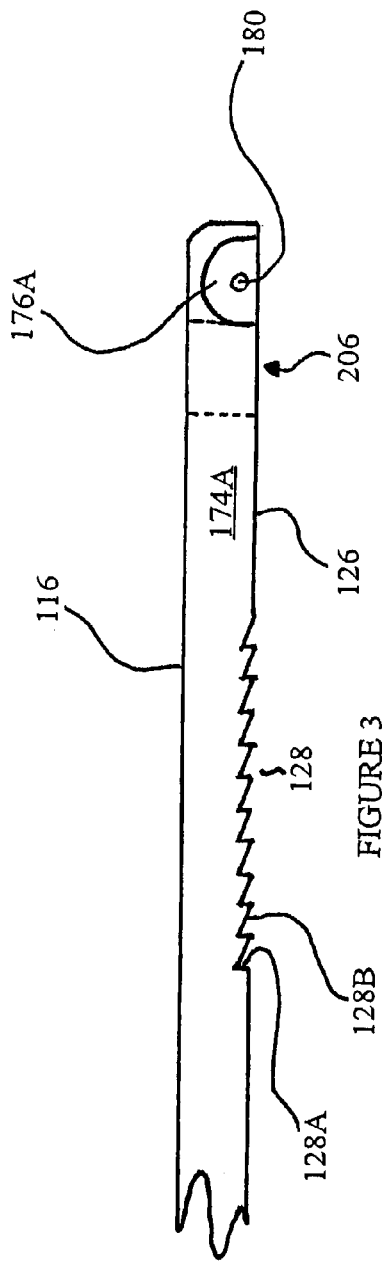
FIG. 3 is a fragmented side elevation view of a portion of the shaft of the FIG. 2 band seating tool.
Figure 4:
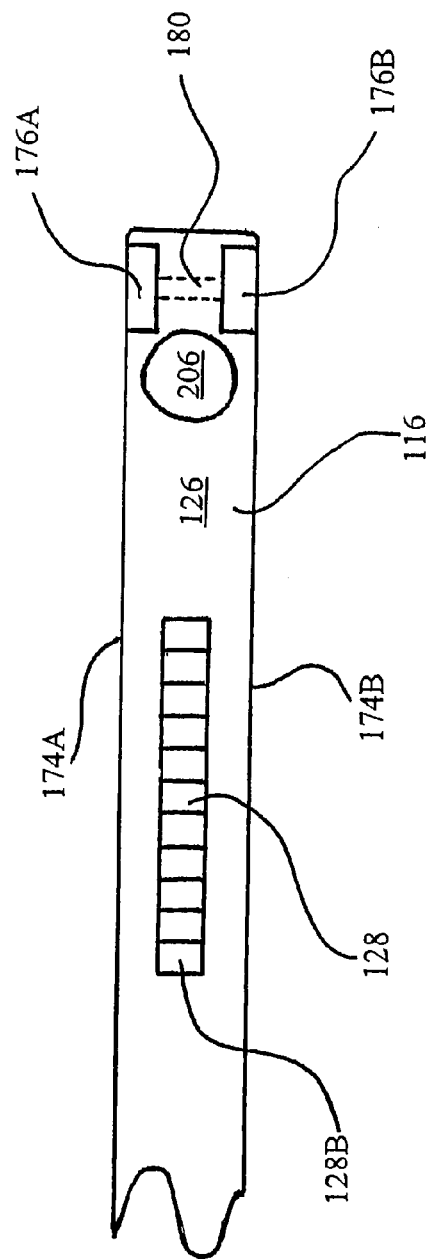
FIG. 4 is a bottom plan view of the FIG. 3 shaft portion.
Figure 7A:
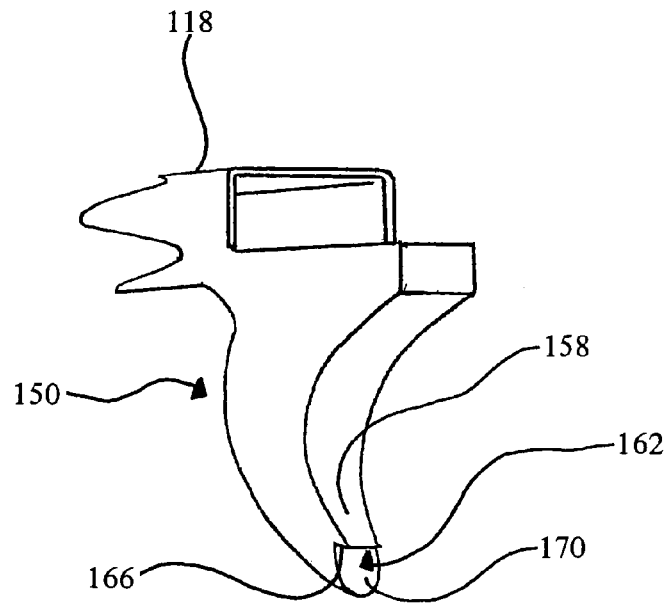
FIGS. 7A and 7B are respectively isometric views of the rearward and forward claw members of the FIG. 2 band seating tool.
Figure 7B:
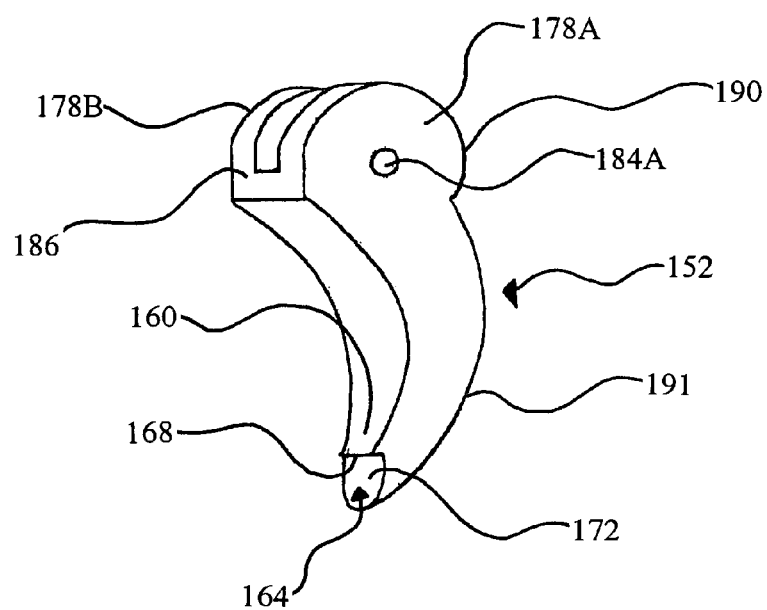

Bottom surface 126 of shaft 116 includes a series of indents 128 which form part of a ratchet mechanism for adjusting and locking the relative longitudinal position of adjustment assembly 119 with respect to shaft 116. As best seen in FIGS. 3 and 4, indents 128 of the illustrated embodiment have a saw-tooth-shape. Preferably, each sawtooth-shaped indent 128 has a vertically oriented surface 128A at its rearward end and an angled surface 128B, which extends at an angle from vertically oriented surface 128A towards its forward end.

Adjustment assembly 119 (best seen in FIGS. 5 and 6) fits slidably over shaft 116 to permit relative longitudinal movement of adjustment assembly 119 with respect to shaft 116. Adjustment assembly 119 includes an adjustment member 118 and a tab 136. In the illustrated embodiment, adjustment member 118 is rectangular in cross-section (to match the cross-sectional shape of shaft 116) and is substantially hollow to define a longitudinally extending bore 130 through which shaft 116 extends. Bottom surface 132 of adjustment member 118 incorporates a slot 134 through which projections 146 extend to engage indents 128 as discussed in more detail below.

Tab 136 (best seen in FIGS. 2 and 5) is coupled to sidewalls 138A, 138B of adjustment member 118 at pivot joint 140. Pivot joint 140 is oriented to permit tab 136 to pivot (or at least deflect) with respect to adjustment member 118 about the transverse axis of pivot joint 140. Tab 136 includes side portions 136A, 136B and a bottom portion 136C. In the illustrated embodiment, a forward portion 142 of bottom portion 136C of tab 136 is coupled to bottom surface 132 of adjustment member 118 by one or more fasteners 144, such as screws, rivets, nuts and bolts and/or any other suitable fasteners. Bottom forward portion 142 of tab 136 may alternatively be welded to bottom surface 132 of adjustment member 118 or formed integrally with adjustment member 118.

Tab 136 comprises one or more projections 146, which project through slot 134 to engage or otherwise cooperate with one or more corresponding indents 128 on bottom surface 126 of shaft 116. Together, projection(s) 146 of tab 136 and indents 128 of shaft 116 provide a ratchet mechanism which facilitates longitudinal movement of adjustment assembly 119 relative to shaft 116 and locking of the longitudinal position of adjustment assembly 119 relative to shaft 116. This in turn facilitates corresponding adjustment of gap 156 between claws 150, 152. In the illustrated embodiment, each of projection(s) 146 is saw-tooth-shaped to conform with saw-tooth-shaped indents 128 of shaft 116. Each saw-tooth-shaped projection 146 has a vertically oriented surface 146A at its rearward end and an angled surface 146B, which extends at an angle from vertically oriented surface 146A towards its forward end. Those skilled in the art will appreciate that the characterization of the saw-tooth shape of indents 128 as indents and the saw-tooth shape of projection(s) 146 as projections is a matter of convenience and that any series of saw-tooth-shaped features may be described as comprising indents and/or projections.

When one or more projection(s) 146 of tab 136 engage corresponding indents 128 of shaft 116, adjustment assembly 119 is locked in position relative to shaft 116. In the illustrated embodiment, the angled surface 146B of a projection 146 abuts against the angled surface 128B of a corresponding indent 128, thereby preventing adjustment assembly 119 from moving in the forward direction relative to shaft 116. Similarly, the vertical surface 146A of a projection 146 abuts against the vertical surface 128A of a corresponding indent 128, thereby preventing adjustment assembly 119 from moving in the rearward direction relative to shaft 116. Those skilled in the art will appreciate that vertical surfaces 128A, 146A of indents 128 and projection(s) 146 provide a relatively large engaging force to prevent relative movement of adjustment assembly 119 in the rearward direction and that angled surfaces 128B, 146B of indents 128 and projection(s) 146 provide a relatively small engaging force to prevent relative movement of adjustment assembly 119 in the forward direction.

Preferably, pivot joint 140 and/or tab 136 is biased such that, in the absence of external forces, projection(s) 146 of tab 136 remain engaged with indents 128 of shaft 116. For example, tab 136 may be deformed slightly when it is coupled to adjustment member 118 at pivot joint 140 and/or at its bottom forward portion 142, such that the resilient restoring force associated with tab 136 tends to force projection(s) 146 into engagement with indents 128. Additionally or alternatively, a spring (not shown) may be connected to pivot joint 140 and/or between tab 136 and adjustment member 118 (or shaft 116), such that the restoration force of the spring tends to force projection(s) 146 into engagement with indents 128. With such a configuration, in the absence of any external forces, the position of adjustment assembly 119 is fixed relative to shaft 116 by the engagement of projections 146 and indents 128.

Tab 136 also has a lever portion 148, which extends outwardly from pivot joint 140. Lever portion 148 may be manipulated by the orthodontist with the same hand used to hold handle 112. By pressing lever portion 148, the orthodontist may cause tab 136 to pivot (or deflect) about pivot joint 140. This pivotal movement of tab 136 tends to move projections 146 away from shaft 116, thereby disengaging projection(s) 146 from indents 128. When projection(s) 146 are disengaged from indents 128, adjustment assembly 119 may be longitudinally translated with respect to shaft 116. An orthodontist using tool 110 may accordingly manipulate tab 136 to adjust the longitudinal position of adjustment assembly 119 with respect to shaft 116 and thereby adjust the width of gap 156 between claws 150, 152. When the desired gap width is achieved, the orthodontist releases lever portion 148, such that projection(s) 146 re-engage indents 128 and adjustment assembly 119 is once again locked in position with respect to shaft 116.

Preferably, the longitudinal dimension of each of indents 128, and projection(s) 146 is sized in a range of 0.1–2.0 mm to facilitate a sufficiently fine longitudinal adjustment between shaft 116 and adjustment assembly 119 and a correspondingly fine longitudinal adjustment of the width of gap 156. Preferably, between 5 and 100 indents 128 are provided to facilitate a sufficiently large range of longitudinal adjustment between shaft 116 and adjustment assembly 119 and a sufficiently large range of adjustment of gap 156. There may be as few as one projection 146 on tab 136. However, it is preferable that tab 136 comprise a series of projections 146, which has a range of 2–10 individual projections.

In the illustrated embodiment, as shown best in FIG. 5, rearward claw 150 is integrally formed on the forward end of adjustment member 118. Rearward claw 150 may alternatively be rigidly mounted at or near the forward end of adjustment member 118 (e.g. by welding or using suitable fastener(s)). In the illustrated embodiment, forward claw 152 is pivotally connected to shaft 116 at pivot joint 154. Pivot joint 154 is discussed in greater detail below.

In the illustrated embodiment of FIGS. 2–11, claws 150, 152 have a concave shape such that end portion 158 of rearward claw 150 and end portion 160 of forward claw 152 curve toward one another. The center of curvature of rearward claw 150 is on the forward side of rearward claw 150. As rearward claw 150 extends away from adjustment member 118, it initially extends in the rearward direction and then, as rearward claw 150 extends further away from adjustment member 118, end portion 158 of claw 150 curves back in the forward direction. The center of curvature of forward claw 152 is on the rearward side of forward claw 152. As forward claw 152 extends away from shaft 116, it initially extends in the forward direction and then, as forward claw 152 extends further away from shaft 116, end portion 160 of claw 152 curves back in the rearward direction. Gap 156 is relatively narrow between end portions 158, 160 and relatively wide between the central portions of claws 150, 152. This geometry ensures that only end portions 158, 160 of claws 150, 152 physically engage the band and that there is room for the tooth to project into gap 156 between claws 150, 152. In alternative embodiments, discussed further below, it is not necessary that the forward and rearward claws be curved, provided that their end portions extend toward one another, such that only the end portions of the forward and rearward claws engage the band.

The inward faces of end portions 158, 160 each comprise a notch-shaped engagement feature 162, 164 for engaging an orthodontic band. In the illustrated embodiment, notches 162, 164 respectively comprise catch ledges 166, 168 and guide surfaces 170, 172. An orthodontic band may be received in notch 162 between catch ledge 166 and guide surface 170 and may be received, on its opposite side, in notch 164 between catch ledge 168 and guide surface 172.

Guide surfaces 170, 172 function to guide and retain the outer surface of an orthodontic band (see outer surface 14 of band 10 in FIG. 1) and may be curved to accommodate the circumference and/or any other curvature in the outer surface of the band. Catch ledges 166, 168 bear against the edge of an orthodontic band (see edge 16 of band 10 in FIG. 1) and may comprise serrated ridges or other features (not shown) that help to grip the edge of the band. Catch ledges 166, 168 may also be curved to accommodate the circumference of the band.

Preferably, guide surfaces 170, 172 have dimensions in a range of 0.5–3 mm corresponding to the thickness of the outer surface of conventional orthodontic bands. Similarly, catch ledges 166, 168 preferably have dimensions in a range of 0.2–1 mm to correspond to the thickness of the edge of conventional orthodontic bands. Preferably, as best seen in FIGS. 9A and 9B, the angle $\Theta_1$ between catch ledge 166 and guide surface 170 and the angle $\Theta_2$ between catch ledge 168 and guide surface 172 are in a range of 30–90 degrees. These angles $\Theta_1$, $\Theta_2$ help to ensure that once the edge of a band is received in notch 162 and/or notch 164, tool 110 does not inadvertently slip off of the edge of the band.

Notches 162, 164 are preferably fabricated from a material that is hard and non-deformable when compared to the material used to form bands. Non-limiting examples of suitable materials include: carbon-based materials; hard metals; steel and other hard metal alloys; and other hard non-metallic materials.

As discussed briefly above, forward claw 152 is preferably pivotally coupled to the forward end of shaft 116 at pivot joint 154. In the illustrated embodiment, as shown best in FIG. 7B, forward claw 152 has a pair of transversely spaced apart lobes 178A, 178B. FIGS. 3 and 4 show side surfaces 174A, 174B of shaft 116 each comprise a cut-out section 176A, 176B for receiving a corresponding one of lobes 178A, 178B. Shaft 116 is penetrated by a transversely extending bore 180. As shown in FIG. 8, transversely extending pivot pin 182 projects through bore 180. Pivot pin 182 and bore 180 are dimensioned to permit pivotal motion of pivot pin 182 about its transverse axis within bore 180. The transverse ends of pivot pin 182 also project into apertures 184A, 184B in lobes 178A, 178B.

Preferably, the transverse ends of pivot pin 182 are fixed to lobes 178A, 178B, such that forward claw 152 pivots with pin 182. Pivot pin 182 may be fixed to lobes 178A, 178B by any suitable means (not shown). Non-limiting examples of means for fixing pivot pin 182 to lobes 178A, 178B include: threaded fasteners (e.g. where shaft 182 is threaded and nuts are used to fix lobes 178A, 178B to shaft 182); transversely extending keys on pivot pin 182 and corresponding slots on apertures 184A, 184B (or keys in apertures 184A, 184B and slots on pivot pin 182); and set screws, which extend through one or more of lobes 178A, 178B and bite into the circumferential surface of pivot pin 182. Those skilled in the art will appreciate that pivot joint 154 shown in the illustrated embodiment and described herein represents merely one of many possible pivot joint implementations. Pivot joints are well understood in the art and the invention disclosed herein should be understood to accommodate any pivot joint implementation.

The pivotal motion of forward claw 152 in pivot joint 154 is limited. Rearward surface 186 of forward claw 152 (see FIG. 7B) abuts against a stop surface 187 (see FIG. 8) on shaft 116 to limit the pivotal motion of forward claw 152 in the rearward direction (i.e. clockwise in FIG. 8). An upper portion 193 of forward surface 190 of forward claw 152 abuts against a stop surface 188 on the forward side of cutout sections 176A, 176B (FIGS. 3 and 4) to limit the pivotal motion of forward claw 152 in the forward direction (i.e. counter clockwise in FIG. 8). Preferably, the maximum angular displacement of forward claw 152 about pivot joint 154 is in a range of 0–10 degrees, such that the corresponding arcuate displacement of end portion 160 of forward claw 152 when it pivots about pivot joint 154 is in a range of 0–2.5 mm.

In the illustrated embodiment, pivot joint 154 is biased by a biasing mechanism 192, which tends to pivot forward claw 152 towards the rearward limit of its pivotal motion (i.e. in the clockwise direction in FIG. 8). In the illustrated embodiment, biasing mechanism 192 comprises a resiliently deformable piece of material, which is fastened to the forward end of shaft 116 by one or more fasteners 195. As shown best in FIG. 8, biasing mechanism 192 applies a restorative spring force against a curved central portion 191 of the forward surface 190 of forward claw 152. The restorative force of biasing mechanism 192 ensures that when tool 110 is used to seat a band, forward claw 152 exerts a force on the band that is oriented in the direction of the arc transcribed by end portion 160 as forward claw 152 pivots about pivot joint 154. This force helps to ensure that notches 162, 164 of claws 150, 152 do not slip off of the band. Preferably, the restorative force of biasing mechanism 192 is strong enough to firmly resist forward pivotal movement of forward claw 152 and to firmly push forward claw 152 rearwardly towards its rest position. Biasing mechanism 192 also ensures that, in the absence of external forces, forward claw 152 is in an orientation where it is ready for use. Those skilled in the art will appreciate that the bias mechanism for applying bias to pivot joint 154 may be implemented using a number of other techniques. Such techniques may involve alternative spring configurations, such as a pair of looped springs coupled to opposing transverse sides of shaft 116 that join one another in a transverse lower portion that contacts forward claw 152 to apply a rearward restorative force, for example.

Figure 2:
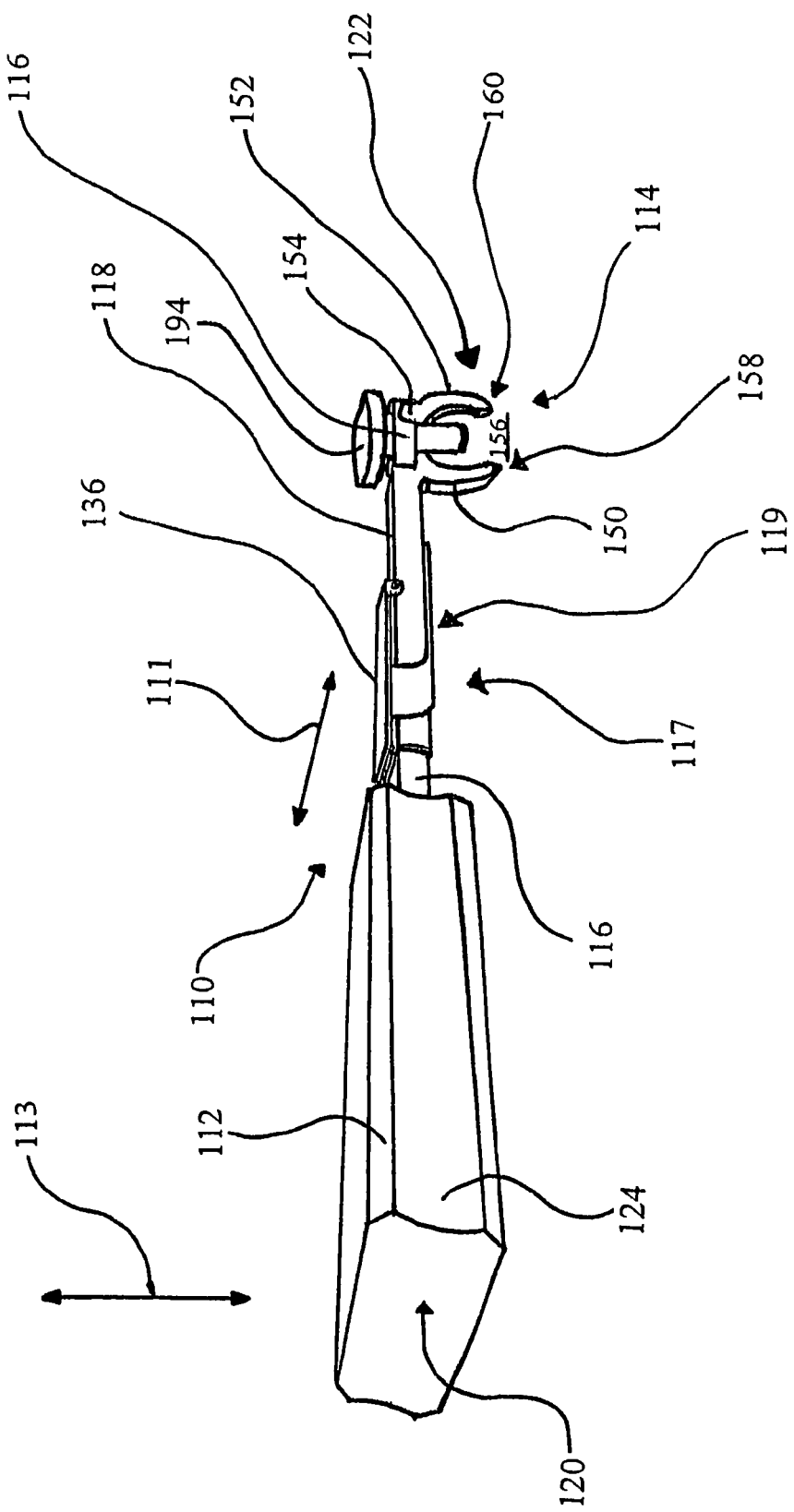
FIG. 2 is a perspective view of a band seating tool according to one embodiment of the invention.
Figure 10:
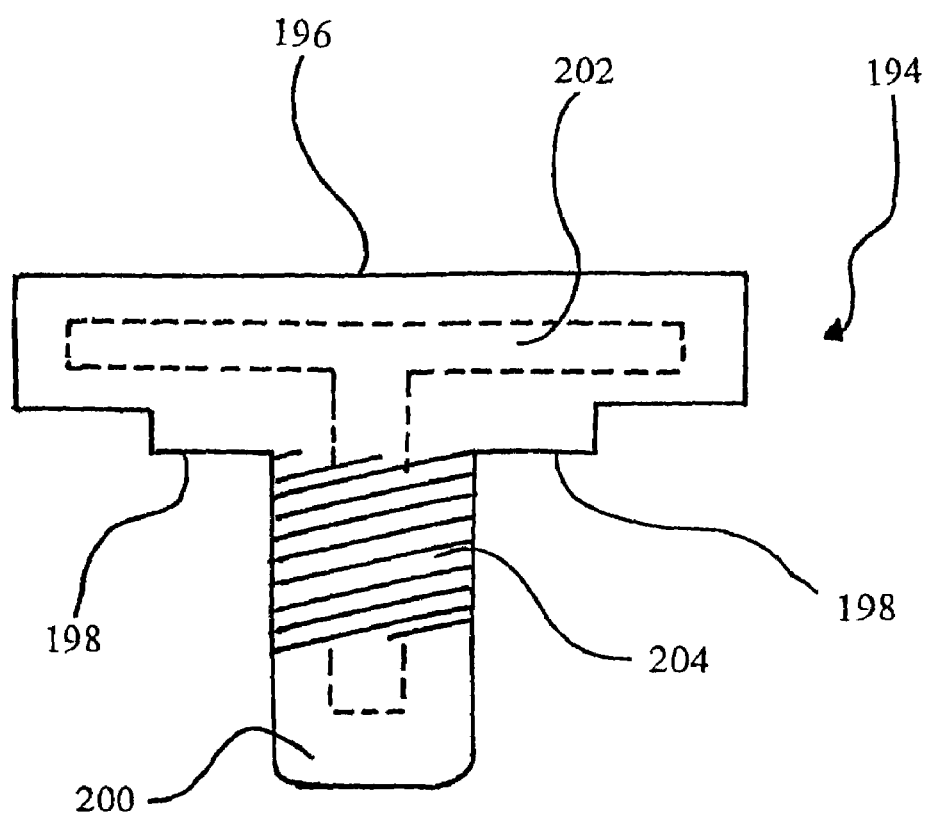
FIG. 10 is a side elevation view of a bite-receiving member of the FIG. 2 band seating tool.

Tool 110 may also include a bite-receiving member 194, which, in the illustrated embodiment of FIGS. 2 and 10, comprises a disc-shaped bite-receiving surface 196, a trunk portion 198 and a safety portion 200. Bite-receiving member 194 is coupled to shaft 116, such that safety portion 200 projects through aperture 206 (FIGS. 3 and 4) in shaft 116 and into gap 156 between rearward and forward claws 150, 152. Safety portion 200 may have threads 204 on its outer surface for engaging corresponding threads (not shown) on the inner surface of aperture 206. Bite-receiving surface 196 and safety portion 200 of bite-receiving member 194 are preferably fabricated in part from a relatively soft material, such as plastic for example. In the illustrated embodiment, bite-receiving member 194 comprises a plastic body which surrounds an internal metal framework 202.

Bite-receiving member 194 functions to receive the patient's biting force (i.e. on bite-receiving surface 196) and to transfer that force through trunk portion 198, through shaft 116 and to claws 150, 152. An orthodontist may use the patient's biting force together with tool 110 to seat an orthodontic band. Safety portion 200 also helps to prevent patient injury if one or both of claws 150, 152 slip off of the edge of the band. In such a circumstance, safety portion 200 will abut against one or more of the patient's teeth and prevent claws 150, 152 from contacting the patient's teeth or gingiva.

Figure 11:
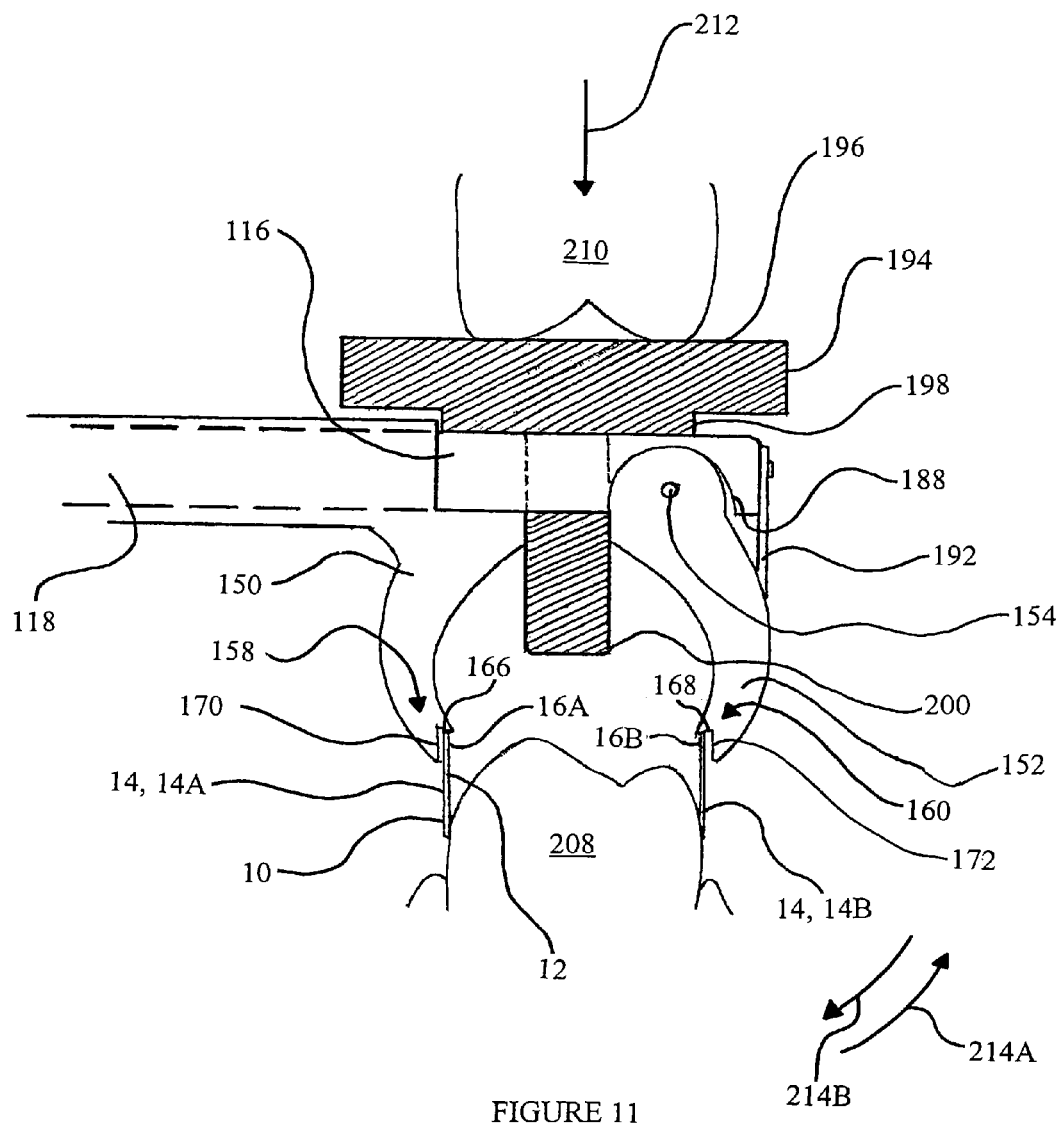
FIG. 11 is a schematic, fragmented side elevation view of the FIG. 2 band seating tool seating a band on a mandibular tooth.

The operation of band seating tool 110 is now explained with reference to FIGS. 1–11. FIG. 11 and the description provided below describe tool 110 in use to seat a band 10 onto a mandibular tooth 208. Those skilled in the art will appreciate that the band seating tool 110 is inverted and operated in a substantially similar manner to seat a band on a maxillary tooth.

An orthodontist selects an appropriately sized band 10 for application to tooth 208. To seat band 10 on tooth 208, an orthodontist uses lever portion 148 of tab 136 to adjust the longitudinal position of adjustment assembly 119 relative to shaft 116 and to thereby adjust gap 156 between claws 150, 152. Gap 156 is selected such that the distance between guide surfaces 170, 172 approximately matches the diameter of outer surface 14 of band 10. The orthodontist then releases lever portion 148, so that projection(s) 146 of tab 136 engage corresponding indents 128 of shaft 116 and adjustment assembly 119 is fixed relative to shaft 116.

Band 10 may initially be placed with finger pressure onto tooth 208. Tool 110 is then positioned in engagement with band 10 such that guide surfaces 170, 172 engage outer surface 14 of band 10 on opposite sides 14A, 14B thereof (i.e. on opposite sides of tooth 208). The orthodontist may then apply a moderate amount of pressure to move claws 150, 152 downward over band 10, such that the opposite sides 14A, 14B of outer surface 14 slide along guide surfaces 170, 172 until the opposite sides 16A, 16B of upper edge 16 abut against catch ledges 166, 168. This may involve a small amount of pivotal movement of forward claw 152 about pivot joint 154.

The patient then bites down such that the occlusal surface(s) of one or more maxillary teeth 210 contact bite-receiving surface 196 of bite-receiving member 194. In the illustration of FIG. 11, the patient's bite force is directed generally downwardly (i.e. in the direction of arrow 212) and corresponding downwardly oriented force is transferred through trunk portion 198 of bite-receiving member 194, through shaft 116, adjustment member 118, claws 150, 152 and catch ledges 166, 168 onto the opposite sides 16A, 16B of edge 16.

The force applied to the opposite sides 16A, 16B of edge 16 moves band 10 downwardly over the outer surface of mandibular tooth 208, thereby seating band 10 on tooth 208. The force applied to the opposite sides 16A, 16B of edge 16 simultaneously prevents band 10 from pivoting around the outer surface of tooth 208. The forces applied to the opposite sides 16A, 16B of edge 16 may be generally parallel to one another. As band 10 moves downwardly over the surface of tooth 208, forward claw 152 may pivot about pivot joint 154 in either or both of the directions of arrows 214A, 214B to accommodate wider and/or narrower portions of tooth 208. The restorative force of biasing mechanism 192 ensures that end portion 160 of forward claw 152 follows the outer surface of tooth 208. By moving handle 112, an orthodontist may alter the orientation of tool 110 and may thereby alter the direction of the forces applied to the opposite sides 16A, 16B of edge 16.

As discussed above, notches 162, 164 include catch ledges 166, 168 and guide surfaces 170, 172 designed to minimize the chance that claws 150, 152 will slip off of band 10. However, in the event that one or both of claws 150, 152 slip off of band 10, downwardly projecting safety portion 200 of bite-receiving member 194 contacts the occlusal surface of tooth 208 (or other mandibular teeth), thereby preventing claws 150, 152 from damaging adjacent teeth or gingiva.

In an alternative method of using tool 110, band 10 may initially be placed between guide surfaces 170, 172 and forward claw 152 may be caused to pivot slightly in the direction of arrow 214A about pivot joint 154, such that biasing mechanism 192 causes band 10 to be retained between guide surfaces 170, 172. Band 10 may then be applied directly to a tooth as described above.

Figure 12:
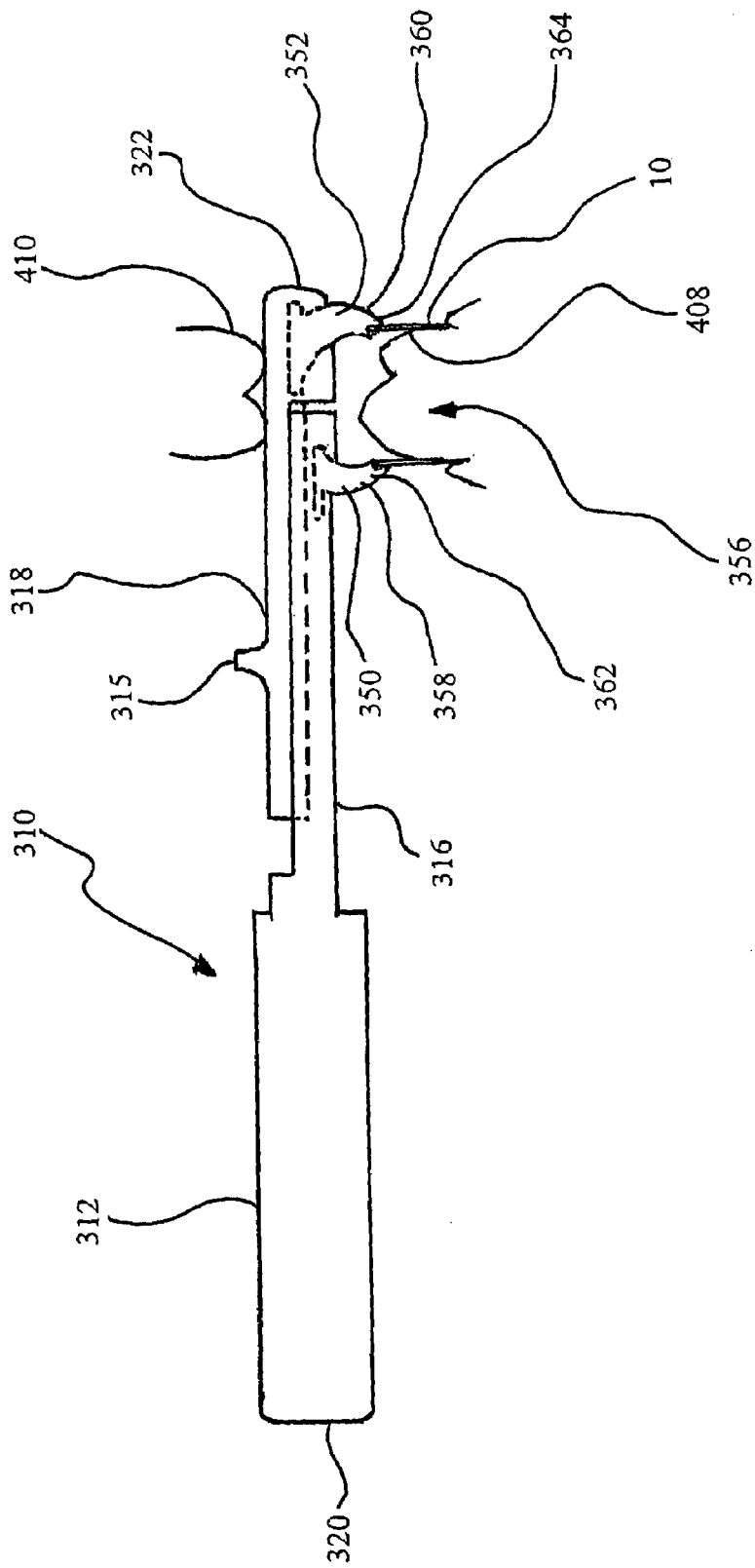
FIG. 12 is a side elevation view of a band seating tool according to an alternative embodiment of the invention.

FIG. 12 is a side view of a band seating tool 310 according to an alternative embodiment of the invention. In most respects, band tool 310 is substantially similar to band tool 110 depicted in FIGS. 2–11 and described above. Features of tool 310 that are similar to features of tool 110 are provided with similar reference numerals preceded by the digit "3" rather than "1" or "2", as the case may be. Features of tool 310 that are substantially similar to features of tool 110 are not discussed in detail in this description.

Tool 310 includes a shaft 316 having and a pair of spaced apart claws 350, 352 at or near one end 322 thereof. Claws have end portions 358, 360 which extend toward one another. More particularly, end portion 358 of rearward claw 350 extends forwardly and end portion 360 of forward claw 352 extends rearwardly. In the illustrated embodiment, claws 350, 352 have concave shapes. Claws 350, 352 may have other shapes, provided that their end portions 358, 360 extend toward one another. Advantageously, when tool 310 is used to seat a band, the extension of the end portions 358, 360 of claws 350, 352 toward one another concentrates and directs force onto the edge of the band and provides the tooth with a place to project as the band is seated.

End portions 358, 360 of claws 350, 352 also comprise engagement features 362, 364 for engaging an edge of a band. Preferably, engagement features 362, 364 are notch-shaped and include catch ledges and guide surfaces similar to those of engagement features 162, 164 described above, wherein the catch ledges engage an edge of a band and the guide surfaces abut against an exterior surface of the band.

Shaft 316 may have handle 312 at an end 320 thereof. Tool 310 may also incorporate an adjustment member 318 for adjusting the size of gap 356 between claws 350, 352. In the illustrated embodiment, adjustment member 318 is slidably coupled to shaft 316 to move longitudinally with respect thereto. Movement of adjustment member 318 relative to shaft 316 causes corresponding adjustment of the size of gap 356. In some embodiments, adjustment member 318 has a range of motion of up to 12 mm relative to shaft 316. In preferred embodiments, adjustment member 318 has a range of motion of up to 8 mm relative to shaft 316. In the illustrated embodiment, adjustment member 318 incorporates a hand operable protrusion 315, which may be used by an orthodontist to adjust and/or maintain the position of adjustment member 318. Protrusion 315 may be replaced by other suitable features, such as buttons, grooves, grips or the like. Tool 310 may comprise a locking mechanism (not shown) which fixes the position of adjustment member 318 relative to shaft 316 and fixes the corresponding size of gap 356.

Unlike tool 110, neither of claws 350, 352 of tool 310 are pivotable with respect to shaft 316. In contrast, claw 350 is rigidly mounted on (or integrally formed with) shaft 316 and forward claw 352 is rigidly mounted on (or integrally formed with) adjustment member 318. Tool 310 also does not comprise a bite member. However, as shown in FIG. 12, band 10 may still be seated on mandibular tooth 408 by the biting force associated with maxillary tooth 410, which is transferred through tool 310 and claws 350, 352 to the edges of band 10.

As will be apparent to those skilled in the art in the light of the foregoing disclosure, many alterations and modifications are possible in the practice of this invention without departing from the spirit or scope thereof. For example:

In the embodiments depicted in FIGS. 2–11 and described above, rearward claw 150 is integrally formed with or rigidly mounted to adjustment member 118. In alternative embodiments, rearward claw 150 is pivotally coupled to adjustment member 118. In other alternative embodiments, both claws 150, 152 are rigidly mounted or integrally formed such that they do not pivot.

In the embodiments depicted in FIGS. 2–11 and described above, indents 128 are located on the bottom surface 126 of shaft 116. In alternative embodiments, indents 128 are located on other surfaces of shaft 116 and engage with correspondingly located projection(s) 146 on tab 136.

Handle 112 is not a required feature of tool 110. In some embodiments, an orthodontist may simply grip a rearward portion of shaft 116.

In the embodiments depicted in FIGS. 2–11 and described above, shaft 116 is described as having a series of indents 128 and tab 136 is described as having one or more projection(s) 146. In alternative embodiments, tab 136 comprises a series of indents 146 and shaft 116 comprise one or more projection(s) 128.

In the embodiments depicted in FIGS. 2–11 and described above, indents 128 and projections 146 are respectively described as being saw-tooth shaped. In alternative embodiments, tool 110 may comprise other adjustment features for adjustably locking the position of adjustment member 118 with respect to shaft 116.

For example, such adjustment features may incorporate one or more "male" projections which project into one or more corresponding "female" apertures; or pairs of surfaces having transversely extending ridges. In still other embodiments, tool 110 may have a locking mechanism which may be locked to fix the position of adjustment member 118 with respect to shaft 116 and released to allow adjustment member 118 to move freely with respect to shaft 116.

In the illustrated embodiments described above, notches 162, 164 represent engagement features for engaging opposite sides of an orthodontic band. In alternative embodiments, the end portions 158, 160 of claws 150, 152 may have alternative engagement features which may include alternative implements for exerting force on the opposing sides of an orthodontic band. For example, alternative engagement features may include one or more projections, indents, hooks or the like.

Figure 13A:
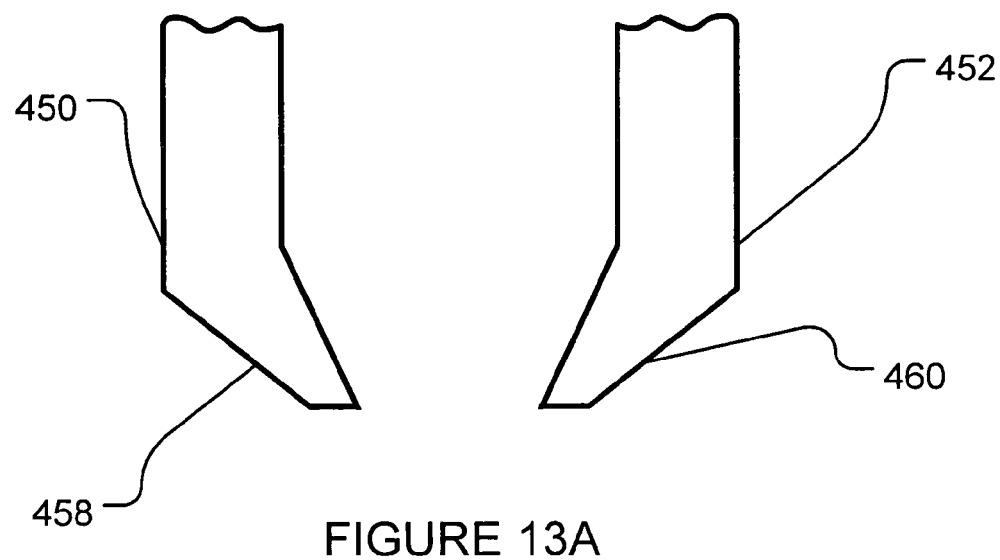
FIGS. 13A–13B are respectively side views of alternatively shaped claw members which may be used in accordance with the invention.
Figure 13B:
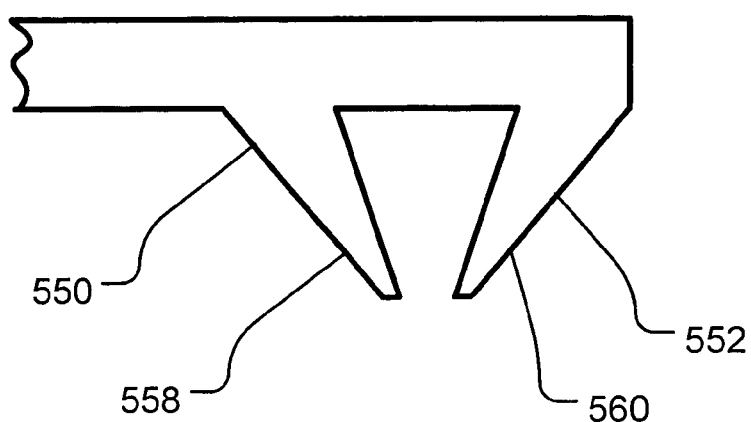

In the embodiments described above, claws 150, 152, 350, 352 are concave shaped, such that their respective end portions 158, 160, 358, 360 extend toward one another. That is, end portions 158, 358 of rearward claws 150, 350 extend forwardly and the end portions 160, 360 of forward claws 152, 352 extend rearwardly. In alternative embodiments, claws 150, 152, 350, 352 need not be concave shaped to have their respective end portions 158, 160, 358, 360 extend toward one another. FIG. 13A shows a pair of claws 450, 452 having end portions 458, 560 that extend toward one another, but which have a non-curved profile. FIG. 13B depicts another pair of claws 550, 552 having end portions 558, 560 that extend toward one another. For the sake of simplicity, details such as engagement features are not shown in the drawings of FIG. 13A, 13B. Those skilled in the art will appreciate that there are many other shapes of claws having end portions that extend toward one another.

In the illustrated embodiment of FIGS. 2–11, bite-receiving member 194 comprises a safety portion 200. Alternative embodiments comprise a separate safety member that projects from shaft 116 between claws 150, 152 and is not related to bite-receiving member 194. Such a safety member functions in substantially the same manner as safety portion 200 of bite-receiving member 194. In other alternative embodiments, safety portion 200 may be interchangeable and may have different lengths.

Tab 136 is not a required feature of the invention. Adjustment member 118 may comprise its own adjustment features which may be selectively engaged and disengaged from corresponding adjustment features of shaft 116. Those skilled in the art will appreciate that there are many adjustment features which may be used to selectively engage with and disengage from shaft 116. Examples of such adjustment features include spring bias mechanisms or latching mechanisms which bias or latch the adjustment features of adjustment member 118 and shaft 116 into engagement with one another, but which may be overcome or unlatched by an orthodontist who desires to adjust the relative position of adjustment member 118 and shaft 116.

Accordingly, the scope of the invention is to be construed in accordance with the substance defined by the following claims.

What is claimed is:

1. An orthodontic band seating tool comprising:
a shaft extending in a longitudinal direction, the shaft comprising a shaft member and an adjustment member, the adjustment member moveably coupled to the shaft member for translational movement in the longitudinal direction relative to the shaft member; and
first and second spaced-apart claws extending away from an end of the shaft, each claw having an end portion further comprising an engagement feature having a surface positionable against an edge of the band; wherein the end portion of the first claw extends toward the second claw and the end portion of the second claw extends toward the first claw;
wherein one of the first and second claws is coupled to each of the shaft member and the adjustment member such that relative movement between the shaft member and the adjustment member in the longitudinal direction causes corresponding relative movement between the first and second claws in the longitudinal direction; and
wherein at least one of the claws is pivotally coupled to the shaft via a pivot joint.

2. A tool according to claim 1 wherein the shaft comprises a first stop surface located to abut against a corresponding first surface of the at least one of the claws when the pivot joint reaches a first angular configuration and to thereby prevent further pivotal movement of the pivot joint in a first angular direction.

3. A tool according to claim 2 comprising a biasing mechanism for applying a bias force to the at least one of the claws, the bias force tending to maintain the pivot joint in the first angular configuration.

4. A tool according to claim 3 wherein the shaft comprises a second stop surface located to abut against a corresponding second surface of the at least one of the claws when the pivot joint reaches a second angular configuration and to thereby prevent further pivotal movement of the pivot joint in a second angular direction.

5. A tool according to claim 1, wherein each engagement feature comprises a notch having a catch ledge for engaging the edge of the band and a guide surface for engaging an outer surface of the band.

6. A tool according to claim 5 wherein the guide surface is concave in a direction transverse to a direction which the claws extend away from the shaft assembly.

7. An orthodontic band seating tool according to claim 1 wherein the shaft member comprises one or more adjustment features for selectively engaging one or more corresponding adjustment features of the adjustment member and thereby locking a position of the adjustment member relative to the shaft member.

8. A tool according to claim 7 wherein the adjustment features on the shaft member and the corresponding adjustment features on the adjustment member are saw-tooth shaped.

9. A tool according to claim 7 wherein the shaft comprises an engagement mechanism having a first configuration wherein the one or more adjustment features of the shaft member engage the one or more corresponding adjustment features of the adjustment member and a second configuration wherein the one or more adjustment features of the shaft member are disengaged from the one or more corresponding adjustment features of the adjustment member.

10. A tool according to claim 1 wherein the claw coupled to the shaft member is pivotally coupled.

11. A tool according to claim 1 wherein each engagement feature comprises at least one of: one or more indents and one or more protrusions.

12. An orthodontic band seating tool comprising:
a shaft;
first and second spaced-apart claws extending away from an end of the shaft, each claw having an end portion further comprising an engagement feature having a surface positionable against an edge of the band; and
a bite-receiving member having a bite-receiving surface for receiving force applied to the tool by one or more opposing teeth of the patient and a trunk portion for transferring the force received on the bite-receiving surface to the claws and their corresponding engagement features;
wherein the end portion of the first claw extends toward the second claw and the end portion of the second claw extends toward the first claw and wherein at least one of the claws is pivotally coupled to the shaft via a pivot joint.

13. A tool according to claim 12 wherein the bite-receiving member comprises a safety portion which extends from the trunk portion, through the shaft assembly and between the pair of claws.

14. An orthodontic band seating tool comprising:
a shaft; and
first and second spaced-apart claws extending away from an end of the shaft, each claw having an end portion further comprising an engagement feature having a surface positionable against an edge of the band;
wherein the end portion of the first claw extends toward the second claw and the end portion of the second claw extends toward the first claw;
wherein the shaft comprises a shaft member and an adjustment member moveably coupled to the shaft member and wherein one of the first and second claws is coupled to each of the shaft member and the adjustment member such that relative movement between the shaft member and the adjustment member causes corresponding relative movement between the first and second claws;
wherein the adjustment member comprises a hand actuatable tab coupled to a pivotal joint, the tab comprising one or more adjustment features for selectively engaging one or more corresponding adjustment features of the shaft member and thereby locking a position of the adjustment member relative to the shaft member;
wherein the tab comprises a lever portion for adjusting the pivotal joint between the tab and the shaft member between a first configuration wherein the one or more adjustment features of the tab engage the one or more corresponding adjustment features of the shaft member and a second configuration wherein the one or more adjustment features of the tab are disengaged from the one or more corresponding adjustment features of the shaft member; and
wherein the pivotal joint between the tab and the adjustment member is biased toward the first configuration.

15. An orthodontic band seating tool comprising:
a shaft extending in a longitudinal direction, the shaft comprising a shaft member and an adjustment member, the adjustment member moveably coupled to the shaft member for translational movement in the longitudinal direction relative to the shaft member; and
first and second spaced-apart claws extending away from an end of the shaft, each claw having an end portion further comprising an engagement feature having a surface positionable against an edge of the band;
wherein the end portion of the first claw extends toward the second claw and the end portion of the second claw extends toward the first claw;
wherein one of the first and second claws is coupled to each of the shaft member and the adjustment member such that relative movement between the shaft member and the adjustment member in the longitudinal direction causes corresponding relative movement between the first and second claws in the longitudinal direction; and
wherein each engagement feature comprises a notch having a catch ledge for engaging the edge of the band and a guide surface for engaging an outer surface of the band.

16. A tool according to claim 15 wherein the first and second claws are concave shaped and the end portion of the first claw curves towards the second claw and the end portion of the second claw curves toward the first claw.

17. A tool according to claim 15 wherein the claw coupled to the adjustment member is integrally formed with the adjustment member.

18. An orthodontic band seating tool according to claim 15 wherein the shaft comprises a ratchet mechanism for locking a position of the adjustment member relative to the shaft member.

19. An orthodontic band seating tool according to claim 15 wherein the adjustment member comprises a hand actuatable tab coupled to a pivotal joint, the tab comprising one or more adjustment features for selectively engaging one or more corresponding adjustment features of the shaft member and thereby locking a position of the adjustment member relative to the shaft member.

20. A tool according to claim 19 wherein the adjustment features on the tab and the corresponding adjustment features on the shaft member are saw-tooth shaped.

21. A tool according to claim 19 wherein the tab comprises a lever portion for adjusting the pivotal joint between the tab and the shaft member between a first configuration wherein the one or more adjustment features of the tab engage the one or more corresponding adjustment features of the shaft member and a second configuration wherein the one or more adjustment features of the tab are disengaged from the one or more corresponding adjustment features of the shaft member.

22. A tool according to claim 15 wherein an angle between the catch ledge and the guide surface is in a range of 30–90 degrees.

23. A tool according to claim 15 wherein a dimension of the guide surface is in a range of 0.5–3 mm.

24. A tool according to claim 15 wherein a dimension of the catch ledge is in a range of 0.2–1 mm.

25. A tool according to claim 15 comprising a safety member which extends from the shaft assembly and between the pair of claws.

26. An orthodontic band seating tool comprising:
   a shaft;
   first and second spaced-apart claws extending away from an end of the shaft, each claw having an end portion further comprising an engagement feature having a surface positionable against an edge of the band; and
   a safety member which extends from the shaft and between the first and second claws;
wherein the end portion of the first claw extends toward the second claw and the end portion of the second claw extends toward the first claw.

27. A tool according to claim 26 wherein at least one of the claws is pivotally coupled to the shaft via a pivot joint.

28. A tool according to claim 26 wherein the shaft comprises a shaft member and an adjustment member moveably coupled to the shaft member and wherein one of the pair of claws is coupled to each of the shaft member and the adjustment member such that relative movement between the shaft member and the adjustment member causes corresponding relative movement between the claws.

29. A tool according to claim 28, wherein each engagement feature comprises a notch having a catch ledge for engaging the edge of the band and a guide surface for engaging a outer surface of the band.

30. A tool for seating an orthodontic band on a tooth of a patient, the tool comprising:
   an elongated shaft assembly; and
   a pair of claws which comprise concave body portions that are spaced apart from one another and which comprise end portions that extend toward one another as the claws extend away from the shaft assembly, the end portion of each claw comprising a corresponding engagement feature for engaging an edge of the band on a corresponding side thereof;
wherein force applied to the tool is transferable to opposite sides of the edge of the band via the corresponding engagement features of the claws;
wherein the concave body portions of the pair of claws are spaced apart sufficiently far that the concave body portions of the claws do not contact the tooth during application of force to the band; and
wherein each engagement feature comprises a notch having a catch ledge for engaging the edge of the band and a guide surface for engaging an outer surface of the band.

31. A tool according to claim 30 wherein the shaft assembly comprises a shaft member and an adjustment assembly moveably coupled to the shaft member and wherein one of the pair of claws is coupled to each of the shaft member and the adjustment assembly, such that relative movement between the shaft member and the adjustment assembly causes corresponding relative movement between the claws.

32. A tool according to claim 31 comprising
   a ratchet mechanism for locking a position of the adjustment assembly relative to the shaft member.

33. A tool according to claim 30 wherein the guide surface is concave in a direction transverse to a direction which the claws extend away from the shaft assembly.

34. A tool for seating an orthodontic band on a tooth of a patient, the tool comprising:
   an elongated shaft assembly; and
   a pair of claws which comprise concave body portions that are spaced apart from one another and which comprise end portions that extend toward one another as the claws extend away from the shaft assembly, the end portion of each claw comprising a corresponding engagement feature for engaging an edge of the band on a corresponding side thereof;
wherein force applied to the tool is transferable to opposite sides of the edge of the band via the corresponding engagement features of the claws;
wherein the concave body portions of the pair of claws are spaced apart sufficiently far that the concave body portions of the claws do not contact the tooth during application of force to the band; and
wherein at least one of the claws is pivotally coupled to the shaft assembly via a pivot joint.

* * * * *